United States Patent [19]
Kasai, deceased et al.

[11] Patent Number: 4,883,452
[45] Date of Patent: Nov. 28, 1989

[54] METHOD OF FABRICATING FROZEN FINE LIVER PIECES FOR ARTIFICIAL LIVER, APPARATUS FOR FREEZING THE SAME, AND FREEZING VESSEL

[75] Inventors: Yoichi Kasai, deceased, by Motoko Kasai, personal representative; Akio Kawamura; Yoshimi Nakanishi; Akira Kakita; Toshihiko Tsuburaya, all of Sapporo; Yasuo Kuraoka; Nobuo Sakao, both of Ibaraki, all of Japan

[73] Assignee: Hoxan Corporation, Sapporo, Japan

[21] Appl. No.: 245,925

[22] Filed: Sep. 16, 1988

Related U.S. Application Data

[63] Continuation of Ser. No. 661,469, Oct. 16, 1984, abandoned.

[30] Foreign Application Priority Data

| Mar. 2, 1984 | [JP] | Japan | 59-30260[U] |
| Mar. 16, 1984 | [JP] | Japan | 59-37534[U] |
| Mar. 16, 1984 | [JP] | Japan | 59-37533[U] |
| Mar. 17, 1984 | [JP] | Japan | 59-6172 |

[51] Int. Cl.$^4$ .................. A61B 19/00; F25D 25/00
[52] U.S. Cl. ........................... 600/36; 128/898; 62/62
[58] Field of Search ............ 62/62, 64, 78, 114; 426/418; 28/1 R, 897, 898; 600/36

[56] References Cited

U.S. PATENT DOCUMENTS

| 3,677,024 | 7/1972 | Segall | 62/64 |
| 3,753,357 | 8/1973 | Schwartz | 62/64 |
| 4,008,754 | 2/1977 | Kraushaur et al. | 62/62 |
| 4,107,937 | 8/1978 | Chmiel | 62/78 |
| 4,117,881 | 10/1978 | Williams et al. | 435/1 |
| 4,155,331 | 5/1979 | Lawrence et al. | 62/64 |
| 4,295,339 | 10/1981 | Kurooka et al. | 62/64 |
| 4,304,293 | 12/1981 | Scheiwe et al. | 62/62 |
| 4,327,799 | 5/1982 | Scheiwe et al. | 62/62 |
| 4,336,691 | 6/1982 | Burstein et al. | 62/64 |
| 4,471,629 | 9/1984 | Toledo-Pereyra | 435/1 |
| 4,539,824 | 9/1985 | Kuraoka et al. | 62/374 |

FOREIGN PATENT DOCUMENTS 3308688 9/1984 Fed. Rep. of Germany .......... 435/1

OTHER PUBLICATIONS

Toledo-Pereyra, *Journal of Surgical Research*, 28, 563-570, 1980.
Toledo-Pereyra, *Journal of Surgical Research*, 32, 75-84, 1982.

Primary Examiner—C. Fred Rosenbaum
Assistant Examiner—Sharon Rose
Attorney, Agent, or Firm—Fleit, Jacobson, Cohn, Price, Holman & Stern

[57] ABSTRACT

A method of fabricating frozen fine liver pieces for an artificial liver which comprises cutting a liver removed from a human being or an animal, from which blood has been removed, into fine pieces of square shape and freezing the liver pieces with helium gas. A freezing apparatus for an artificial liver which has gas phase pressurizing means for pressurizing liquid helium coupled to a chamber for storing the liquid helium, a helium gas conduit dipped in the liquid helium passed through the chamber to be closed and contained, to which the liver fine pieces are telescopic, and an exhaust conduit provided with a control valve coupled to the freezing chamber. And, a freezing vessel for an artificial liver which has a flow conduit capable of being coupled to an upper portion and a lower portion of a unit, an upper coupling port and a lower coupling port respectively formed therethrough to close plugs, two or more mesh plates laterally laid elevationally in the unit, an exit opened corresponding to a containing chamber thus formed.

2 Claims, 6 Drawing Sheets

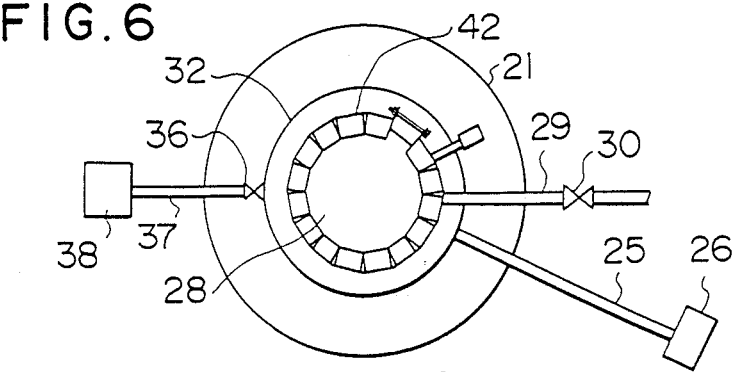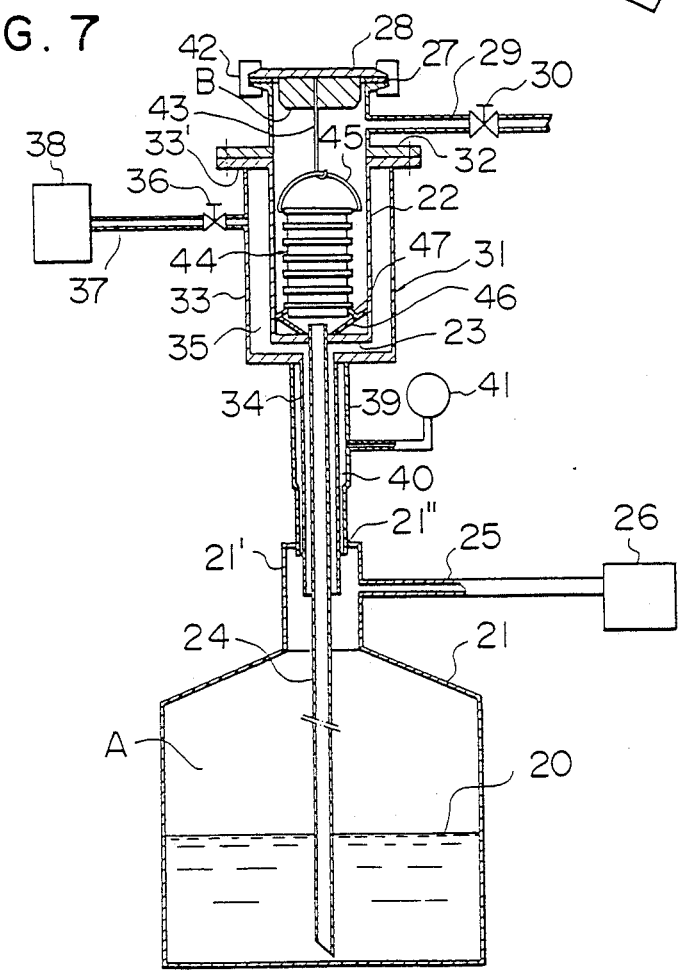

ined States Patent 4,883,452

METHOD OF FABRICATING FROZEN FINE LIVER PIECES FOR ARTIFICIAL LIVER, APPARATUS FOR FREEZING THE SAME, AND FREEZING VESSEL

This application is a continuation of application Ser. No. 661,469, filed Oct. 16, 1984, now abandoned.

BACKGROUND OF THE INVENTION

This invention relates to an artificial liver adapted for an artificial liver supplementing apparatus used for subsidizing the function of the liver of a patient who has a liver disease such as a severe hepatitis and, more particularly, to a method of fabricating frozen fine liver pieces capable of preserving the frozen liver, an apparatus for freezing to execute the same method, and a freezing vessel for fabricating the same.

There is, heretofore, a biological artificial liver which utilizes the living liver of an animal (a dog) retained in a living body as the above-described artificial liver, but such a liver should be provided in the vicinity of a patient (the dog). A dialysis of blood has already been carried out with a cellophane membrane, a PAN membrane, a cation exchange resin, an activated charcoal, an albumin or a hydron as a nonbiological artificial liver, but such dialysis can only supplement the latter of the metabolic function and the detoxicating function of the liver, thereby resulting in unsatisfaction in the results of the therapy.

Therefore, it has been tried to employ an artificial liver used from a living liver excised externally from an animal. However, when the liver of a dog or a pig is used in this manner, the immunological difference between the liver of the dog or pig and a human being is large. A large result cannot be expected even in this case. The liver of a baboon has less such problems, but the probability of obtaining the liver of the baboon is difficult.

It is heretofore known that the liver has its function even in the state that the liver loses its normal state as an organ and finely divided into tissues or individual cells. From this standpoint, the human or animal's livers of sliced state are already used as artificial liver.

In this case, it is required that the artificial liver can endure against the preservation for a long period of time and can be thawed and used as required.

To this end, the above-described artificial liver is frozen for the preservation, but this method includes removing blood, slicing the excised liver in the millimeter order of thickness, and freezing the sliced livers with liquid nitrogen. When the artificial livers thus obtained are thawed used for the artificial auxiliary liver device, its urea producing function and glucose producing function as the liver of the artificial livers are extremely smaller than the case that fresh liver is used, finished in a short time, and cannot be expected for sufficient practical effects.

SUMMARY OF THE INVENTION

An object of the present invention is to provide a method of freezing a liver, which can eliminate the aforementioned drawbacks and disadvantages, can endure against the preservation for a long period of time and can sufficiently exhibit the functions of the liver at the thawed and used time, and advantageously has cutting a liver removed from a human being or an animal, from which blood has been removed, into fine pieces of square shape an freezing the liver pieces with helium gas.

Another object of the present invention is to provide an apparatus for freezing a liver piece, which can uniformly, rapidly and instantaneously inject helium gas to the entire liver pieces in case of executing the aforementioned method, thereby efficiently and regularly freeze the liver piece at the moment to obtain a frozen liver piece capable of exhibiting preferable liver functions at the thawing time.

Still another object of the present invention is to provide a freezing vessel capable of being used to freeze by the aforementioned method.

More particularly, the freezing vessel of the invention contemplates to eliminate the difficulties of inconvenience that mere vessel cannot obtain desirable result in the instantaneous freezing required particularly for the liver pieces, the quantity of liver pieces contained once in the vessel is limited, cannot be largely increased or decreased, cannot preserve the frozen liver nor be useful for the use after thawing time and another implement must be employed.

The above and other related objects and features of the invention will be apparent from a reading of the following description of the disclosure found in the accompanying drawings and the novelty thereof pointed out in the appended claims.

BRIEF DESCRIPTION OF THE DRAWINGS

FIG. 6 is a plan view of an essential section of a freezing apparatus according to a second embodiment of the present invention;

FIG. 7 is a front view partly cut out of the apparatus;

DESCRIPTION OF THE PREFERRED EMBODIMENTS

A method of freezing a liver piece according to the present invention will be described in detail by a first embodiment using a dog with reference to the accompanying drawings. An abdomen is incised in a normal size, the portal vein of the liver is exposed, approx. 1000 ml. of heparin-added Ringer's lactate solution of 4° C. is flowed through a tube internally engaged with the vein, the vena cava in the upper part of the liver is then excised, and the liver is excised.

Then, the liver is dipped in an electrolyte out of cells equivalent to the above Ringer's lactate solution simultaneously when the liver is excised, and the liver is then removed from the solution. Preferably, the liver is cut to squares having approx. 3 to 5 mm per side in the solution without removing from the solution, thereby producing a number of liver fine pieces.

The liver fine pieces are frozen not by liquid nitrogen nor liquid helium but by helium gas. The freezing means may include various mechanisms such as, for example, placing the liver fine pieces in a predetermined closed cavity, and injecting helium gas evaporated from liquid helium to the liver fine pieces in the closed cavity preferably at a considerably high speed.

Thus, the liver fine pieces are instantaneously frozen, and the frozen liver fine pieces thus provided are dipped in low temperature liquefied gas such as liquid nitrogen prepared separately for preservation.

Figure 1:
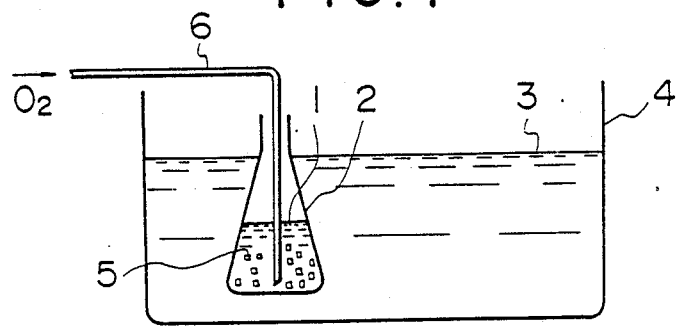
FIG. 1 is an explanatory longitudinal sectional front view of an embodiment of an apparatus used for thawing an artificial liver obtained by an embodiment of a method of the invention and for measuring the liver functions.

In order to measure the function of the liver as the thawed artificial liver for the frozen liver fine pieces preserved as described above, a flask 2 containing 100 m. of 5%-fructose phosphoric acid buffer solution is introduced into a constant-temperature oven 4 for storing hot water 3 of 38° C. as shown in FIG. 1, 30 g. of frozen liver fine pieces 5 frozen by 100 m. of helium gas are filled in the buffer solution 1, 0.1 mg. of ammonium chloride per 1 g. of the liver is filled as a load, and oxygen gas $O_2$ is applied into the solution in the flask 2 through a gas feed conduit 6.

Figure 2:
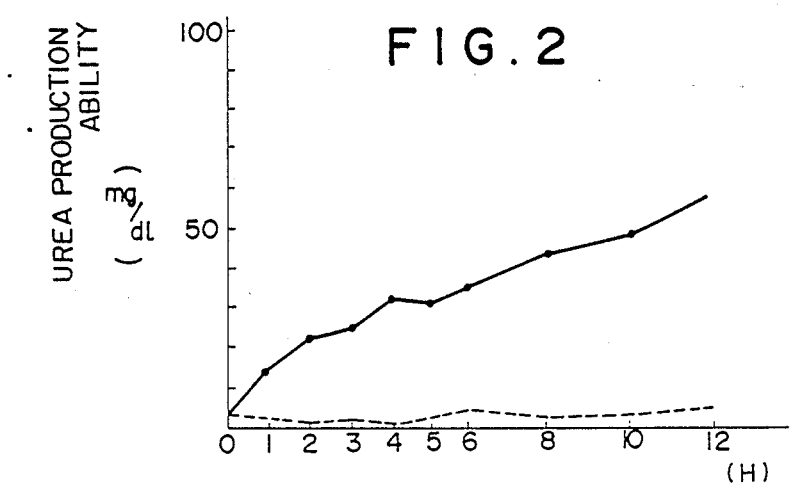
FIGS. 2 and 3 are graphs respectively illustrating the measured results of urea producing function and glucose producing function obtained by the measuring apparatus.
Figure 3:
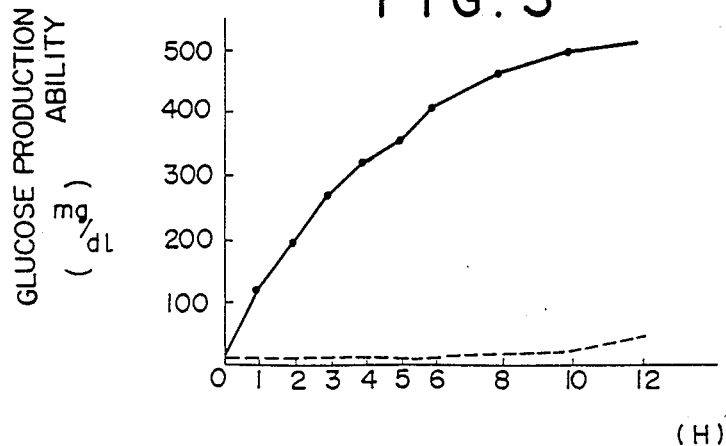

The measured results of the urea nitrogen and glucose are respectively shown in FIGS. 2 and 3. Solid lines show the curves of the measured results of the frozen liver fine pieces obtained by the method according to the present invention, and broken lines show the curves of the measured results of the conventional frozen liver fine pieces A sliced from the liver into thin pieces as shown in FIG. 4(a) and frozen by $LN_2$.

When the urea production ability of the liver shown in FIG. 2 is first observed, remarkable ability is exhibited as compared with the case of the conventional frozen liver fine pieces A, the liver acts sufficiently the urea production ability up to 12 hours after the thawing (i.e., 2 mg./g. liver/12 hours in average), and this exhibited that this result is considerably near 4.1 mg./g. liver/24 hours of the urea production ability of the sliced fresh liver having 1 mm of thickness.

Further, as to the glucose production ability shown in FIG. 3, much preferable result is obtained as compared with the conventional example in the same manner as the urea production ability, the liver continuously acts sufficiently the glucose production ability to 12 hours after the thawing, and could be confirmed to produce 17 mg./g. liver/12 hours.

Figure 4A:
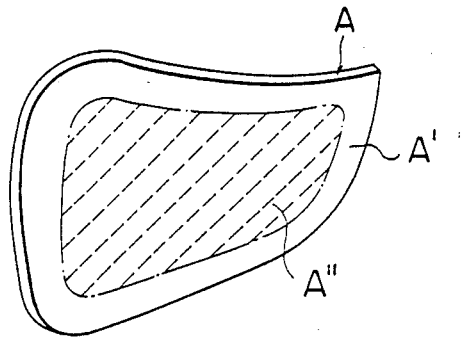
FIGS. 4(a) and 4(b) are explanatory perspective views showing artificial livers according to prior art and the present invention.
Figure 4B:
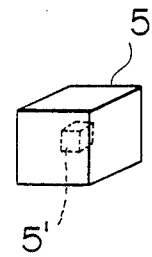

The reasons why the frozen artificial liver provided according to the present invention results in excellent auxiliary liver functions as described above are because the liver is not merely sliced into large thin pieces as in FIG. 4(a) by the conventional method but the liver is finely cut into cubes, rectangular prisms or triangular pyramids shown in FIG. 4(b). Thus, only the outer periphery A' of the conventional liver in FIG. 4(a) serves to perform the liver functions, but the central portion A' which occupies the considerably proportion of the entirety shown by the hatched lines does not participate in the liver functions. On the other hand, slight corners of the central portion 5' of the square liver fine pieces of the present invention do not serve to perform the liver functions as shown in FIG. 4(b), and when the blood flow is executed by the artificial auxiliary liver device, the contacting area with the blood of the liver of the invention advantageously increases.

Figure 5:
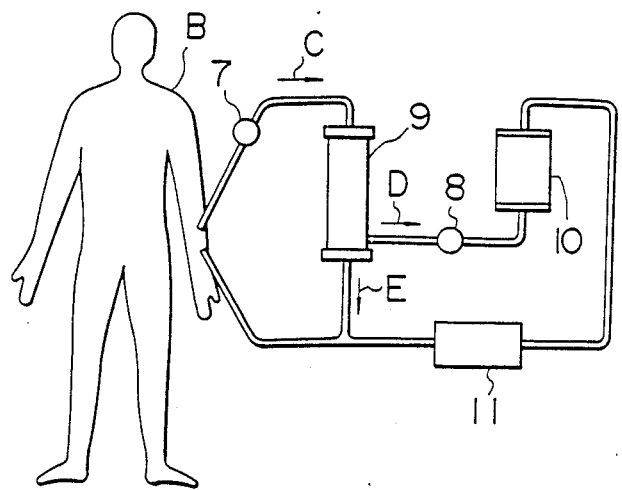
FIG. 5 is an explanatory view showing an example of an artificial auxiliary liver device employing artificial liver.

An example of the artificial auxiliary liver device is shown in FIG. 5. As shown in FIG. 5, the auxiliary liver device is used in parallel with the artery of a patient B. Reference numerals 7 and 8 designate pumps. All blood C is separated into blood-plasma D and blood corpuscle component E by a blood-plasma separator 9. After the blood-plasma D passes the thawed artificial liver contained in a column 10, the blood-plasma D is returned together with the blood corpuscle component to a human body through an artificial dialyzer 11 in this example.

Factors that the liver of the present invention results in excellent functions are points that square liver fine pieces are frozen, and not liquid helium but helium gas is employed using neither liquid nitrogen nor nitrogen gas.

More particularly, the helium gas is considerably low temperature such as −260° C., has 5.23 (kJ/kg.K) of specific heat, which is approx. five times the nitrogen gas, with the result that it is considered that the liver can be frozen without destroying the tissue of the liver by utilizing the fact that the freezing velocity is very large such as 1,000° C./min.

According to the present invention as exemplified in the first embodiment, the liver is cut into square fine pieces, and the square liver fine pieces are frozen by the helium gas. Therefore, the liver can retain sufficiently the same liver functions as the fresh liver to 12 hours after the thawing. Further, since the liver is cut into square fine pieces, the liver fine pieces can be not only readily frozen, but also serve to readily and rapidly perform the liver functions even after the thawing. In addition, since the liver can be easily handled as compared with the conventional sliced large thin pieces, the liver is convenient in the constitution of the artificial auxiliary liver device, and can be preserved permanently with refrigerant such as liquid nitrogen.

An apparatus for freezing a liver as a second embodiment of the present invention will now be described in detail with reference to FIGS. 6 and 7. In FIGS. 6 and 7, a chamber 21 for storing liquid helium 20 and a freezing chamber 22 disposed above the chamber 21 are provided so that a lower end port is dipped in the liquid helium 20 through the chamber 21, and coupled via a helium gas conduit 24 passed through the bottom plate 23 of the freezing chamber 22 at the upper end port.

Gas phase pressurizing means 26 such as a compressor is coupled from an upper port 21' through a pressurizing conduit 25 to the chamber 21, and the internal pressure of the gas phase unit A of the chamber 2 can be accordingly raised by operating the pressurizing means 26.

Then, the freezing chamber 22 can be closed by a cover 28 with a packing 27, a control valve 30 is interposed at an exhaust conduit 29 coupled to the upper peripheral side, and an adiabatic insulator 31 is sheathed on the freezing chamber 22 and the helium gas conduit 24 as will be described in more detail.

More specifically, a flange 33' of an adiabatic outer tank 33 is mounted on a flange 32 projected from the peripheral side of the freezing chamber 22, the helium gas conduit 24 is movably engaged with an outer tank conduit 35 fastened to the bottom opening of the tank 33, and the lower end of the conduit 34 is sealingly fastened to a helium gas conduit 34, thereby forming an adiabatic gap 35 between the freezing chamber 22 and the outer peripheral side of the conduit 24 exposed with the outer atmosphere. Then, a vacuum pump 38 is provided through a vacuum evacuating conduit 37 provided with a control valve 36 at the outer tank 33, thereby exhausting gas in the gap 35.

Further, in the embodiment exemplified in FIGS. 6 and 7, an opening 21' provided at the upper port 21" of the chamber 21 and a bottom plate of the tank 33 are coupled via a conduit 39 sheathed on the conduit 34, thereby communicating between a gap 40 between the conduit 39 and the conduit 34 and the gas phase unit A of the chamber 21, and a pressure gauge 41 for measuring the internal pressure of the gas phase unit A is coupled to the conduit 39.

To employ the freezing apparatus thus constructed, liver fine pieces a, a,.. thus finely divided are contained in the freezing chamber 22, and the chamber 22 is closed. In this case, the cover 28 with a packing 29 is used to close the freezing chamber 22. To fasten the cover 28, the cover 28 is clamped by a clamping chain 42 to the freezing chamber 22 as shown in FIGS. 6 and 7. Prior to this clamping, a hanger 45 of a freezing vessel 44 is engaged with a vertical hook rod 43 from an adiabatic insulator B fastened to the cover 28, the vessel 44 is contained in the freezing chamber 22, and the vessel 44 is placed on placing stable arm bases provided in predetermined number at a conical support 46 fastened to the bottom plate 23 of the freezing chamber 22.

Figure 8A:
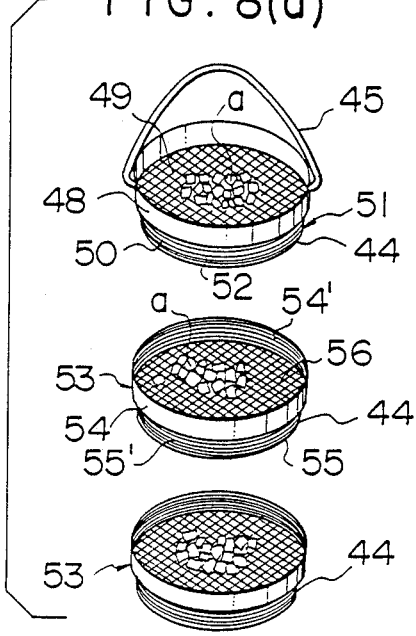
FIGS. 8 and 9 show different vessels used for the apparatus, wherein (a)'s illustrate exploded perspective views and (b)'s illustrate assembled perspective views.
Figure 8B:
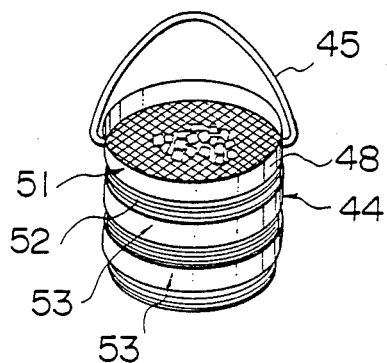

The vessel 44 may employ various types, and examples of the vessel 44 are shown in FIGS. 8 and 9.

In FIG. 8, a middle mesh bottom 49 is extended on a main cylinder 48 provided with the hanger 45, a main tray 51 is formed by protruding a small integral cylinder 50 of small diameter from the cylinder 48 downwardly, and a threaded part 52 is formed on the outer peripheral wall of the cylinder 50 in the example exemplified in FIG. 8.

Further, as apparent in FIG. 8(a), integral trays 53, 53,.. of desired number are prepared. The tray 53 is provided integrally with a large-diameter portion 54 and a small-diameter portion 55. The threaded part 52 of the tray 51 is engaged with the threaded part 45' formed on the inner peripheral surface of the large-diameter portion 54, and the threaded parts 55' formed on the outer periphery of the small-diameter portions 55 of the trays 53, 53,.. of required number are sequentially engaged with the threaded part 54' of the large-diameter portion 53 of next stage, thereby associating the vessels 44 in a manner capable of being disassembled as shown in FIG. 8(a). Then, middle mesh bottoms 56 are respectively extended also on the trays 53, 53,.. and liver fine pieces a, a,.. to be frozen are placed on the middle bottom 56 and the middle mesh bottom 49 of the tray 51 therein.

Figure 9A:
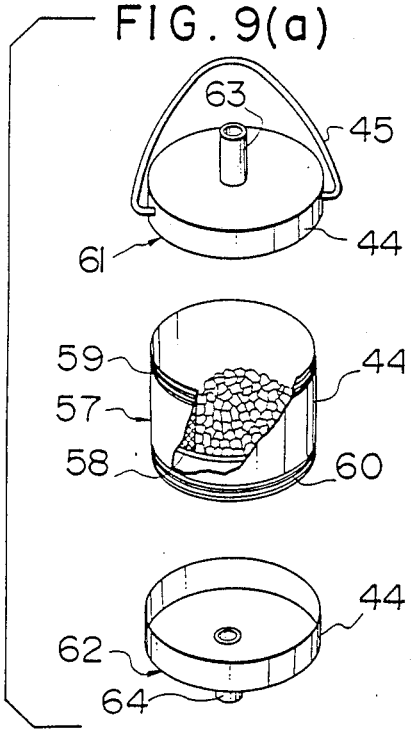
Figure 9B:
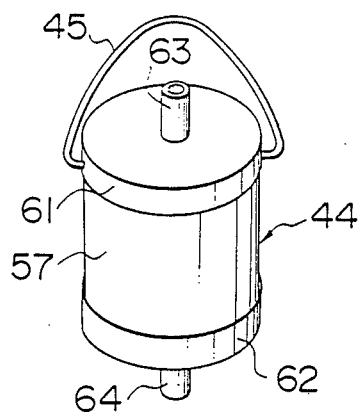

Then, the freezing vessel 44 exemplified in FIG. 9 will now be described in detail. A mesh bottom board 58 is extended on the bottom of a vessel body 57 shown in FIG. 9(a), and the liver fine pieces a, a,.. are contained in the vessel body. Threaded parts 59 and 60 are respectively formed on the upper and lower outer peripheries of the body 57, an upper cover 61 formed with the hanger 45 is engaged with the threaded part 59, and a lower cover 62 is engaged with the threaded part 60. Thus, the freezing vessel 44 shown in FIG. 9(b) is constructed. An outflow cylinder 63 and an inflow cylinder 64 are respectively protruded longitudinally from the centers of the upper and lower covers 61 and 62 to pass helium gas to the vessel 44 as will be described in detail.

As described above, the freezing vessel 44 which has readily contained liver fine pieces a, a,.. cut in square of several mm in side is mounted in the freezing chamber 22, the chamber 22 is closed by the cover 28 as described above, the pressurizing means 26 is operated to raise the internal pressure of the chamber 21 to a predetermined pressure (e.g., approx. 600 mmAg), and the pressure is confirmed by the pressure gauge 41.

In this case, the vacuum pump 38 is naturally operated in advance, to evacuate the gap 35 in vacuum state, thereby enabling to sufficiently perform the adiabatic effect.

When the internal pressure of the chamber 31 is raised to a predetermined pressure as described above, the control valve provided in the conduit 29 is manually or automatically opened, and the conduit 29 is opened with the outer atmosphere.

Thus, helium is gasified from the surface of the liquid helium in the conduit 24, and raised. After the freezing chamber 22 is filled with the helium gas, the helium gas is exhausted from the conduit 29 thus opened into the atmosphere. Then, the liver fine pieces a, a,.. contained in the freezing chamber 22 are instantaneously frozen in contact with the helium gas in this case.

As exemplified by the above-described second embodiment of the apparatus of the invention, the gas phase pressurizing means 26 for pressurizing the liquid helium 20 is coupled to the chamber 21 for storing the liquid helium 20, the helium gas conduit 25 dipped in the liquid helium 20 is passed through the chamber 21 to allow the conduit 24 to communicate with the freezing chamber 22 to be closed and contained, to which the liver fine pieces a, a,.. are telescopic, and the exhaust conduit 29 provided with the control valve 30 is coupled to the freezing chamber 22. Therefore, the helium gas abruptly gasified from the liquid helium and incoming to the freezing chamber 22 for containing the liver fine pieces a, a,.. is supplied to and passed through the freezing chamber 22. Thus, the helium gas can be rapidly and uniformly contacted with the liver fine pieces contained in the freezing chamber 22. Therefore, the liver fine pieces can be uniformly frozen instantaneously at the helium temperature, and are frozen with necessary and sufficient consumption amount of the helium gas. Consequently, a freezing apparatus which has no waste of helium gas can be provided.

Figure 10:
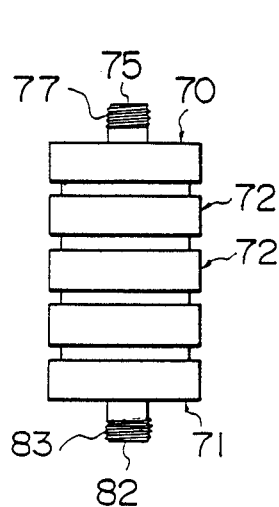
FIG. 10 is a front view of a freezing vessel according to a third embodiment of the invention.

A third embodiment as a freezing vessel used to execute the method of the first embodiment of the invention will now be described in detail with reference to FIGS. 10 to 12. The vessel is slightly similar to that in FIG. 9, but this vessel is composed at least of a cover unit 70 and a bottom unit 71, as well as one or more of coupling cylinder units 72, 72,.. associated between the cover unit 70 and the bottom unit 71, which may be preferably formed of members made of synthetic resin such as Teflon.

The cover unit 70 is formed of a ceiling plate 73, and a peripheral side wall 74 in a tray shape, an upper coupling port 75 is passed at the center of the ceiling plate 73, and the port 75 is closed by a mesh plate 76 bonded to the inner surface of the ceiling plate 73.

The coupling port 75 as exemplified in the drawings is protruded upwardly from the ceiling plate 73, an integral threaded part 77 of male threads are formed thereon, a plug 78 is threaded with the threaded part 77 as designated by a dotted chain line in the drawings to close the port 75, or a flow conduit, not shown, used to flow to be described later may be threaded to couple therebetween. In this case, it is noted naturally that the threaded part 77 may be formed of female threads, and the port 75 may not always be protruded but be formed in recess, or further may be coupled by mere engagement without providing the threaded part 77.

A lower coupling portion 79 is provided at the peripheral side wall 74. In the exemplified example in the drawings, the coupling portion 79 is formed of female threads, and the bottom unit 71 or the coupling cylinder units 72, 72 are detachably coupled thereto as will be described in detail.

Figure 11:
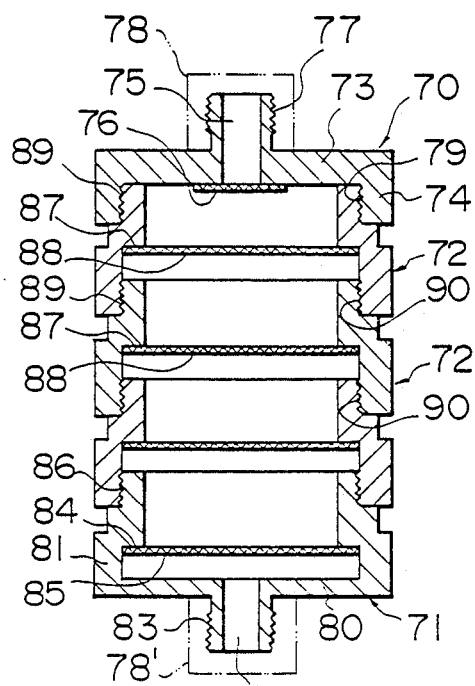
FIG. 11 is a longitudinal sectional front view of the vessel.
Figure 12:
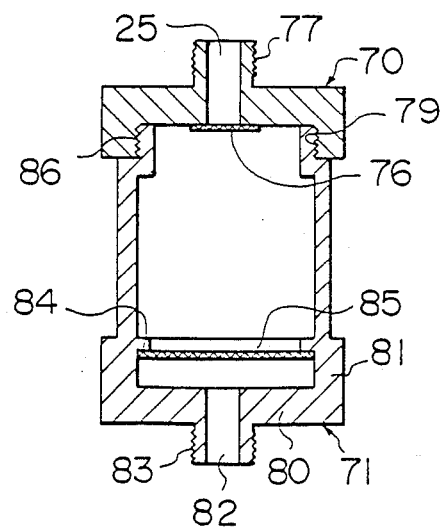
FIG. 12 is a longitudinal sectional front view of the vessel in another used state.

Then, the bottom unit 71 is formed of a bottom plate 80 and a peripheral side wall 81 as apparent in FIGS. 11 and 12, a lower coupling port 82 is provided through the center of the bottom plate 80. In the embodiment exemplified in the drawings, the coupling port 82 is protruded downwardly similar to the coupling port 75, a coupling threaded part 83 is formed on the outer periphery thereof, and a plug 78' or a flow conduit may be coupled thereto.

Further, a lower stepwise edge 84 is formed on the middle inner surface of the side wall 81, the unit 71 is formed elevationally by a mesh plate 85 for placing in contact with the edge 84, and an upper coupling portion 86 is formed of male threads on the outer periphery with the upper end of the side wall 81 formed in a small diameter.

The cylinder units 72, 72,.. used as required are formed in a cylindrical shape, a mesh plate 88 for placing is bonded to the lower stepwise edge 87 formed in the middle height in the same manner as the case of the bottom unit 71, is elevationally formed in the cylinder units 72, an upper coupling portion 89 of male threads is formed on the upper outer periphery reduced in diameter, and a lower coupling portion 90 of female threads is formed on the lower inner periphery of the same diameter as the coupling portion 89.

To employ this, the liver fine pieces to be frozen are placed on the mesh plate 85 for placing of the bottom unit 71, and the lower coupling portion 79 of the cover unit 70 is threaded with the upper coupling portion 86 of the bottom unit 71 in FIG. 12.

In this case, it is noted that the coupling portions 79, 86 may not be threaded, but a mere engagement may be formed. Refrigerant such as gas helium may be introduced into the vessel by coupling a refrigerant supply conduit, not shown, to the lower coupling port 82, and is then discharged from the upper coupling port 75, and the liver fine pieces on the placing mesh plate are instantaneously frozen entirely in contact with the refrigerant in this case.

In case of FIG. 11, the cover unit 70 is not coupled directly to the bottom unit 71, but a lower coupling portion 90 of the cylinder unit 72 is threaded with an upper coupling portion 86, the liver fine pieces are contained also on the placing mesh plate 72 of the unit 72, and the coupling portion 90 of the other cylinder unit 72 is threaded with the upper coupling portion 89 of the cylinder unit 72, thereby coupling the two cylinder units 72 in double manner to thread the cover unit 70 with the cylinder unit 72 of the uppermost stage, In this case, four times the liver fine pieces of FIG. 12 may be simultaneously frozen.

In this case, the mesh plate 76 prevents the liver fine pieces from being discharged from the upper coupling port 75 by the refrigerant injected from the lower coupling port 82.

When the liver fine pieces are thus frozen completely as described above, the plugs 78, 78' are respectively engaged with the upper and lower coupling ports 75, 82. In this state, the liver fine pieces are filled in a preservation unit such as by liquid nitrogen for preservation.

When the frozen liver fine pieces thus preserved as described above are further to be used; the plugs 78, 78' are removed, the frozen liver fine pieces are thawed by predetermined means. Then, flow conduits in the artificial auxiliary liver device are respectively coupled to the upper and lower coupling ports 75, 82, and the auxiliary liver device is then operated to pass the patient's blood to the liver pieces and to then return the blood to the patient.

As exemplified in the third embodiment of the freezing vessel according to the present invention, the freezing vessel comprises the cover unit 70 formed of the ceiling plate 73 and the peripheral side wall 74 in such a manner that the upper coupling port 75 closed by the mesh plate 76, capable of being coupled with the flow conduit and being closed by the plug 78 is formed through the ceiling plate 73, the cover unit 70 formed with the lower coupling portion 79 at the peripheral side wall 74, the coupling cylinder unit 72 formed elevationally by the placing mesh plate 88 laterally provided, and provided with the lower coupling portion 79 of the cover unit 70, the detachable upper coupling portion 89 and the lower coupling portion 90, and the bottom unit 71 formed of the bottom plate 80 and the peripheral side wall 81 in such a manner that the flow conduit is provided capable of being coupled to the bottom plate 80 with the lower coupling port 82 capable of being closed by the plug 78', elevationally formed of the placing mesh plate 85 laterally provided in the peripheral side wall 81, and provided with the upper coupling portion 86 detachable from the lower coupling portion 89 or the cover unit 70 or the lower coupling portion 89 of the coupling cylinder unit 72. Therefore, the refrigerant can be rapidly contacted with the liver fine pieces on the placing mesh plate by discharging the refrigerant introduced from the lower coupling port 82 from the upper coupling port 75, and the liver fine pieces can be desirably frozen instantaneously.

Further, the quantity of the liver fine pieces to be frozen once can be increased or decreased by coupling only the cover unit 70 and the bottom unit 71 or by interposing the coupling cylinder units 72 in the desired number. Particularly in case of using the liver fine pieces after thawing as described above, the flow of the blood can be controlled corresponding to whether the patient is adult or child who used the artificial auxiliary liver device as increased or decreased as described above. Further, for preservation or transportation, the vessel can be readily handled conveniently by the use of the plugs 78, 78'. The frozen liver fine pieces might not be unintentionally discharged from the vessel by arranging the mesh plate 76, and can be used by connecting the vessel to the artificial auxiliary liver device. Consequently, the vessel for another purposes is not necessarily prepared.

A fourth embodiment of the freezing vessel according to the present invention will be described in detail with reference to FIGS. 13 to 16. A unit 100 formed in a cylinder made of synthetic resin such as Teflon is formed respectively with an upper coupling port 103 and a lower coupling port 104 at the centers of the upper and lower portions 101 and 102 therethrough.

In the embodiment exemplified in the drawings, the coupling ports 103 and 104 are not only protruded upwardly and downwardly, but coupling threaded parts 105 and 106 are respectively formed as ale threads on the outer peripheries thereof. Thus, in case that blood is flowed to be described later, a flow conduit is coupled by threading to the coupling ports 103, 104 or plugs 107, 107' are engaged as designated by one-dotted chain lines in FIG. 14, and can be closed. In this case, it is noted that the coupling threaded parts 105, 106 are not formed, but a mere engagement means may be employed for coupling therebetween, or the threaded parts 105, 106 may be formed as female threads in the same manner as the third embodiment as described above.

Figure 13:
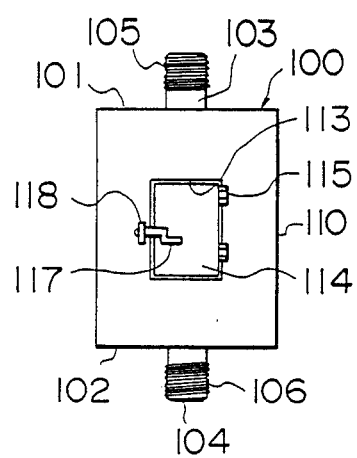
FIG. 13 is a front view of the freezing vessel according to a fourth embodiment of the invention.
Figure 14:
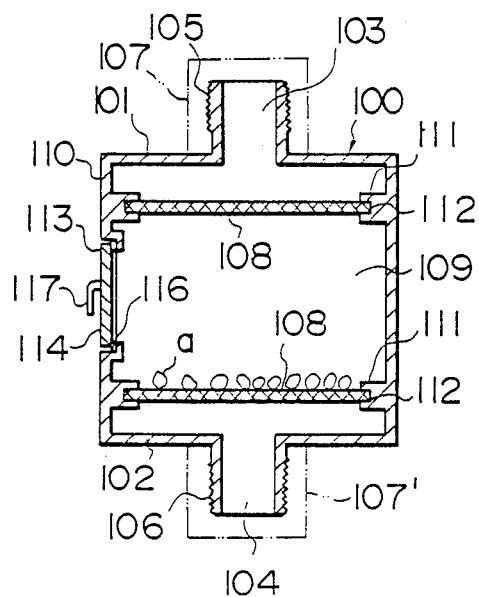
FIG. 14 is a front longitudinal sectional view of the vessel.

In the unit 100, two or more mesh plates 108, 108,.. may be laid elevationally, thereby forming containing chambers 109 of predetermined number. In FIGS. 13, 14, a containing chamber 109 is formed of only two mesh plates 108, 108. However, in the embodiment in FIG. 15, five mesh plates 108; 108,.. are laterally laid to form four containing chambers 109, 109,..

Figure 16:
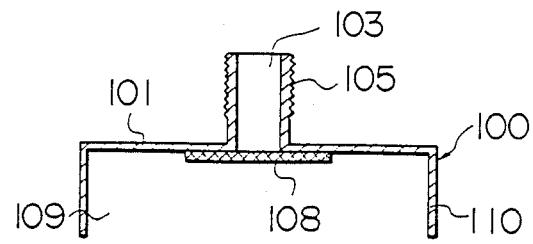
FIG. 16 is a front longitudinal sectional view showing the upper portion of the vessel of different embodiment of the invention from FIG. 2.

As laterally laying means of the mesh plates 108, 108, as exemplified in the drawings, the mesh plates 108, 108 are engaged with the supporting grooves 112 of the supporting projecting strips 111 111,.. projected on the inner surface of the peripheral side wall 110 of the unit 100. In this case, since the mesh plate 108 of the uppermost stage does not place the liver fine pieces a, a,.. thereon as will be described later, the mesh plate 108 may employ, as shown in FIG. 16, a small mesh plate may be bonded fixedly on the upper inner surface of the unit 100 to close the upper coupling port 103.

Further, in this embodiment, exits 113 may be opened at the position corresponding to the containing chambers 109, 109,..., and a cover 114 openably closed on the exit 113 may be provided.

Figure 15:
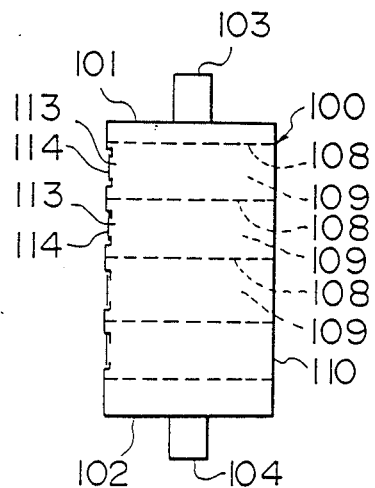
FIG. 15 is a front longitudinal sectional view showing the other used state of the vessel.

In the embodiment exemplified in the drawings, the cover 114 is pivotally secured by one or more hinges 115. Reference numeral 116 designates a sealing member. Thus, in FIG. 14, one cover 114 is provided, while in FIG. 15, four covers are respectively provided in the chambers 109, 109. In FIG. 15, reference numeral 117 designates a handle for operating the cover 114, and reference numeral 118 designates an engaging piece projected from the peripheral side wall 110 to hold the handle 117 in closed state by engaging by rotating the handle 117.

To use the freezing vessel of this embodiment, the cover 114 is opened, the liver fine pieces a, a,.. to be frozen are introduced from the exit 113, placed on the mesh plates 108, 108,.. except the mesh plate of the uppermost stage, the cover 114 is then closed, and a refrigerant supply conduit, not shown, is coupled to the lower coupling port 104.

Thus, the refrigerant such as gaseous helium is introduced into the unit 100, and then discharge from the upper coupling port 102 externally. In this case, the liver fine pieces a, a,.. on the mesh plates 108, 108,.. are instantaneously frozen entirely in contact with the refrigerant.

At this time even in any of the freezing vessels in FIGS. 14 and 15, the mesh plate of the uppermost stage serves to perform prevention of unintentional discharge of the liver fine pieces on the mesh plates 108 from the upper coupling port 103 due to the refrigerant injected from the lower coupling port 104.

As described above, when the freezing of the liver fine pieces is finished, the plugs 107, 107' are engaged with the upper and lower coupling ports 102, 104 as shown in FIG. 14, the liver fine pieces may be preserved in a preservation unit, for example, with liquid nitrogen in this state, or may be removed, transported or carried.

Further, when the frozen liver fine pieces thus frozen and preserved as described above are to be used, the plugs 107, 107' are removed, the frozen liver fine pieces are thawed by predetermined means, and a flow conduit of the artificial auxiliary liver device is coupled to the upper and lower coupling ports 103, 104 as described above, thereby operating the device. Thus, the patient's blood is passed to the liver fine pieces, and can be returned to the patient.

In the fourth embodiment exemplified in the drawings, the flow conduit is capable of being coupled to the upper portion 101 and the lower portion 102 of the unit 100, the upper coupling port 103 and the lower coupling port 104 are respectively formed therethrough to close the plugs 107, 107', two or more mesh plates 108, 108',.. are laterally laid elevationally in the unit 100, the exit 113 is opened corresponding to the containing chamber 109 thus formed, and the exist 113 is capable of being opened by the cover 114 Therefore, the refrigerant introduced from the lower coupling port 104 is discharged from the upper coupling port 103, thereby enabling to contact the refrigerant with the liver fine pieces on the mesh plates. Consequently, the liver fine pieces can be instantaneously frozen as desired.

Further, the flow conduit or the plugs 107, 107' are coupled with the coupling ports 103, 104. Thus, to use the liver fine pieces after thawing, the vessel may be connected to the artificial auxiliary liver device as it is for use. The handling of the vessel is convenient by the use of the plugs 107, 107' for the preservation or transportation, and the liver fine pieces might not be unintentionally discharged even by the mesh plate of the uppermost stage.

What is claimed is:

1. A method of fabricating frozen fine liver pieces for an artificial liver comprising:
   cutting a liver removed from a human being or an animal, from which blood has been removed, into fine pieces of cubic shape and size of about 3 to 5 mm per side,
   placing the liver fine pieces in a closed cavity, and
   instantaneously freezing the liver pieces by introducing into the closed cavity at high speed and freezing velocity of about 1000 degrees C./min. helium gas evaporated directly from a source of liquid helium.

2. The method as claimed in claim 1, wherein the liver is obtained by removing the blood from the liver, flowing cell electrolyte such as Ringer's lactate from a portal vein of the liver exposed before excision, and then cutting vena cava in the upper part of the liver.

* * * * *